United States Patent [19]

Blackburn et al.

[11] Patent Number: 4,499,187

[45] Date of Patent: Feb. 12, 1985

[54] METHOD FOR EVALUATING MUTAGENICITY

[75] Inventors: Gary R. Blackburn, Washington Crossing, Pa.; Carl R. Mackerer, Pennington, N.J.; Ceinwen A. Schreiner, Newtown, Pa.

[73] Assignee: Mobil Oil Corporation, New York, N.Y.

[21] Appl. No.: 575,361

[22] Filed: Jan. 30, 1984

[51] Int. Cl.$^3$ .......................... C12Q 1/04; C12Q 1/29
[52] U.S. Cl. .......................................... 435/34; 435/29
[58] Field of Search ..................................... 435/29, 34

[56] References Cited

U.S. PATENT DOCUMENTS 4,256,832  3/1981  Findl et al. ............................ 435/29
4,299,915  11/1981  Thilly et al. .......................... 435/34

Primary Examiner—Sam Rosen
Attorney, Agent, or Firm—Alexander J. McKillop; Michael G. Gilman; Dennis P. Santini

[57] ABSTRACT

A method is provided for rapidly and reliably determining the potential carcinogenic activity of hydrocarbon mixtures which is especially useful for those of petroleum origin. A sample of the mixture is extracted with dimethylsulfoxide (DMSO). An inoculum of *Salmonella typhimurium* tester strain T98 is incubated in the presence of an aliquot of the extract together with an optimal amount of induced rat liver homogenate S9. The excessive production of revertant colonies is a measure of the mutagenic activity of the oil, and this measure is shown to correlate with dermal carcinogenic activity.

11 Claims, 3 Drawing Figures

LEGEND

△ = EXAMPLE 5
□ = EXAMPLE 11
○ = EXAMPLE 12
● = EXAMPLE 15

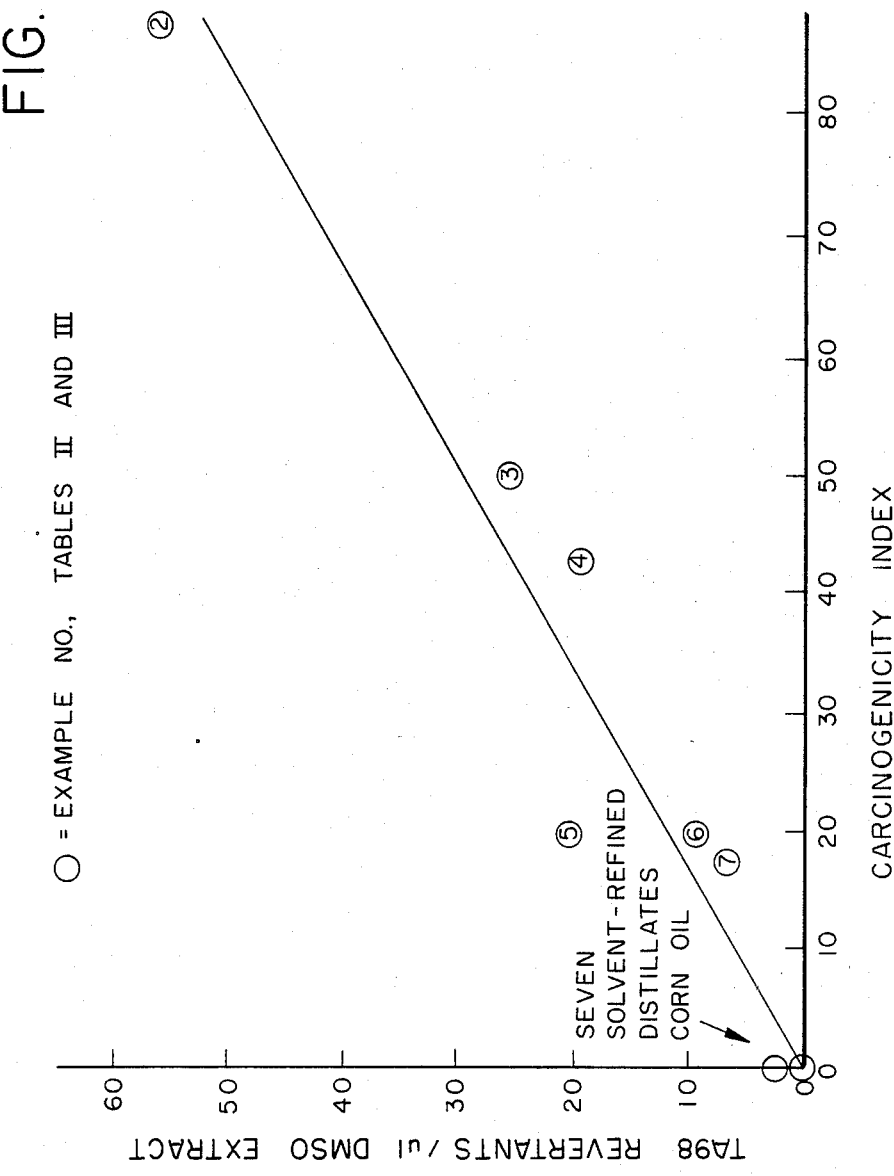

METHOD FOR EVALUATING MUTAGENICITY

FIELD OF THE INVENTION

This invention is broadly concerned with evaluating the carcinogenic activity of hydrocarbons. It is particularly concerned with evaluating the carcinogenic activity, if any, of mixtures of hydrocarbons such as are encountered in a petroleum refinery, and the fuels and lubricant products produced therefrom. It is more particularly concerned with a rapid method for assaying the mutagenic character of such hydrocarbon mixtures.

BACKGROUND OF THE INVENTION

The generally accepted method for evaluating the carcinogenic activity of petroleum products involves animal tests in which animals such as mice are exposed to the hydrocarbon by painting a portion of the skin repeatedly over a long period of time, and evaluating the tendency of such exposure of produce malignant growths. It is generally recognized that this test method requires seventy to eighty weeks of exposure to produce reliable results, and therefore that the method is not suited for situations in which a quick indication of potential carcinogenic activity is required.

In vitro mutagenic activity assays, such as, for example, the Salmonella Microsomal Activation Assay described by B. N. Ames, J. McCann, and E. Yamasaki in *Mutat. Research*, 31, 347–364 (1975), hereinafter referred to as the "Ames test procedure", provide a rapid, inexpensive method for screening chemicals for carcinogenic potential. The entire content of this publication is incorporated herein by reference as if fully set forth. In general, the predictability of this assay with simple chemicals is good; validation studies have produced a 65–90% correlation between mutagenic activity and carcinogenic activity for many relatively pure compounds. However, the assay is unsuited to the testing of water insoluble complex mixtures, such as the complex hydrocarbon mixtures encountered in petroleum refinery streams. Attempts to use the Ames test procedure with such materials give results which are not reproducible and do not relate in a significant way to the known carcinogenic activity index for previously tested mixtures.

It is an object of this invention to provide a reproducible method for assaying the mutagenic property of complex hydrocarbon mixtures. It is a further object of this invention to provide a reproducible mutagenic assay method which shows a strong correlation with the carcinogenic activity index of hydrocarbon mixtures. It is a still further object of this invention to provide a rapid routine method for evaluating the potential carcinogenic activity of petroleum hydrocarbon mixtures. These and further objects of this invention will become evident to one skilled in the art on reading this entire specification and appended claims.

BRIEF DESCRIPTION OF THE INVENTION

It has now been found that a complex hydrocarbon mixture such as a petroleum refinery stream or product may be rapidly and reliably evaluated for possible carcinogenic activity by extracting the hydrocarbon mixture with a suitable solvent, such as dimethylsulfoxide (DMSO), and subjecting an inoculum of a histidine deficient mutant strain of *Salmonella typhimurium* to incubation in the presence of an aliquot of said extract together with, as metabolic activator, an optimal amount of liver homogenate, and thereafter counting the revertant colonies so produced, all as further described hereinbelow.

BRIEF DESCRIPTION OF THE DRAWING

FIG. 3. Correlation of mutagenicity and dermal carcinogenicity.

PREFERRED EMBODIMENTS AND BEST MODE

Figure 1:
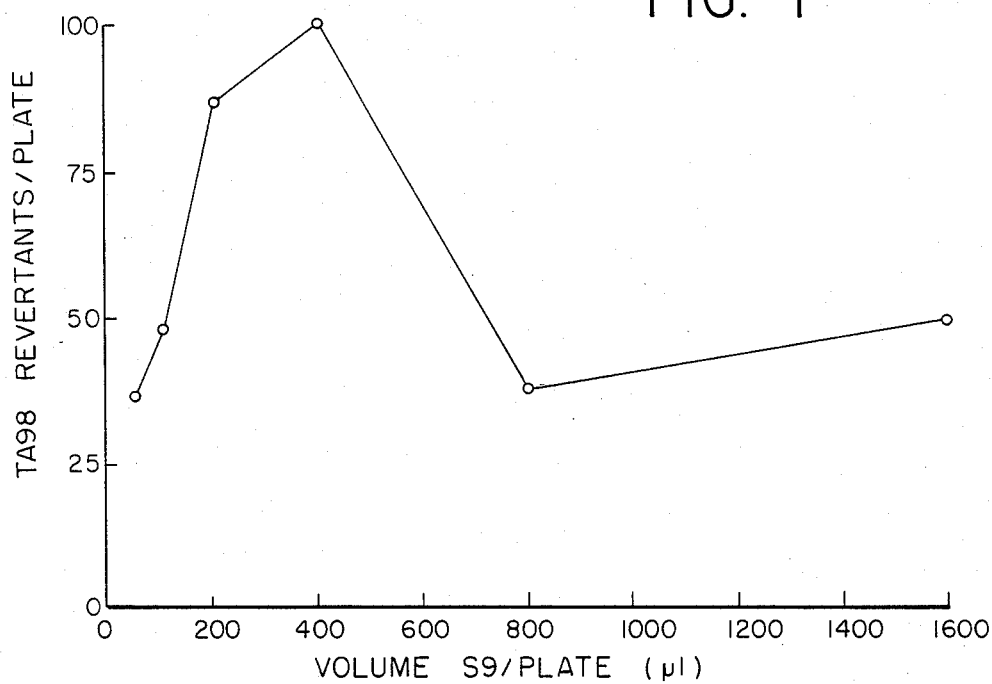
FIG. 1. Mutagenicity of DMSO extract of weakly carcinogenic oil with different levels of S-9.

The preferred embodiments of the method of this invention including the best mode known to us will now be described.

The hydrocarbon mixture to be assayed is extracted with an equal volume of DMSO five times, and the extracts are combined. The combined extract, which serves as surrogate for the hydrocarbon itself, is assayed using *Salmonella typhimurium* tester strain TA98 together with Aroclor 1254-induced rat liver S9. Prior to use, the rat liver S9 homogenate, obtained from Litton Bionetics, Kensington, Md., was stored at −80° C., and thawed on ice for 4 hours prior to use.

The assay is conducted by first introducing into a series of sterile capped culture tubes up to about eight different doses of the combined extract. The doses, usually in the range of 10 to 75 microliters, are selected to delimit the linear portion of the doseresponse curve. Duplicate or triplicate tubes are prepared for each dose level. This is followed by 0.5 ml S9 mix containing 400 $\mu$l S9, 8 $\mu$M $MgCl_2$, 33 $\mu$M KCl, 5 $\mu$M glucose-6-phosphate, 4 $\mu$M NADP and 100 $\mu$M sodium phosphate (pH 7.4), and 0.1 ml *Salmonella typhimurium* broth culture ($1 \times 10^9$ cells/ml). The cultures are incubated at 37° C. with agitation for 20 minutes, following which top agar (0.6% agar, 0.5% NaCl, 0.5 mM histidine-biotin) is added. The tubes are vortexed to ensure adequate mixing and the contents overlaid on 30 ml Vogel-Bonner minimal media plates. Plates are incubated inverted at 37° C. in the dark and revertant colonies are counted 48 hours later.

Spontaneous reversion rates ($47 \pm 8.5$) and negative (solvent) control rates ($47 \pm 8.5$) were determined for all tests. Positive controls were 2-aminoanthracene (2 $\mu$g/plate; $441 \pm 285$ revertants) and benzo[a]pyrene (5 $\mu$g/plate; $839 \pm 434$ revertants).

Specific mutagenic activity is assessed from the slope of the linear portion of the dose response curve that is obtained, and may be reported as revertants per $\mu$l of extract.

Although DMSO is the presently preferred solvent for extracting the hydrocarbon mixture, it is contemplated that other solvents such as 1-methyl-2-pyrollidinone and N,N-dimethyl formamide may prove useful.

The procedure described above is directly applicable to evaluating liquid hydrocarbon mixtures. Less tractable hydrocarbon mixtures, such as asphalts, may be evaluated by dissolving the sample in cyclohexane followed by extraction with DMSO.

It is also contemplated that the preparation of the combined extract described above may be varied somewhat by changing the solvent to oil ratio, the number of extractions, or both, without departing from the teaching of this invention, which requires the use of an extract as surrogate for the hydrocarbon mixture. Although the histidine-deficient *Salmonella typhimurium* tester strain TA98 originally developed by B. N. Ames at the University of California, Berkelely, is particularly preferred, it is contemplated that other histidinedeficient strains of the organism such as TA100 may be useful.

The procedure described above differs from the Ames test procedure not only in the use of extract as surrogate, but also in the use of about eight times the conventional concentration of the induced S9 liver homogenate, judged to be optimal for adequate sensitivity with a wide range of petroleum hydrocarbons. Both of these departures are believed to be necessary to give mutagenic activity assays that are reproducible and correlate well with carcinogenic activity tests.

It is important to note that any mention herein of S9 liver homogenates refers to Aroclor 1254-induced S9, it having been found by us that non-induced S9 is ineffective in the method of this invention. The optimum amount of this component is determined from a series of tests made with a weakly carcinogenic hydrocarbon mixture, illustrated in Example 1 below. The optimum is the approximate amount of S9 effective to produce the optimal increase on revertant count. In Example 1 this is judged to be about 400 μl S9/plate, or about eight times the amount used in the Ames test method. This same amount is used for testing all other hydrocarbon samples with the rat liver homogenate.

As will be illustrated later by example, other sources of metabolizing enzymes may be used, such as induced hamster liver S9 homogenate, either with or without a concomitant increase in the level of vitamin cofactor.

Preparation of the rat and hamster liver homogenates is not described herein, these being well known to those skilled in the art.

The examples which follow illustrate the invention. However, they are not to be interpreted as limiting the scope thereof, which scope is defined by the appended claims and the entire content of this specification.

EXAMPLE 1

An assay of the mutagenic activity of a 100″ hydrotreated heavy naphthenic distillate was made by solvent extracting the oil and subjecting the extract to the assay described above under "preferred embodiments", including the use of 400 μl S9. Parallel assays were performed with the use of 50 μl, 100 μl, 200 μl, 800 μl, and 1600 μl of the S9 homogenate, without a corresponding change of cofactor concentrations. The results are shown in FIG. 1 of the drawing. There is a very large increase in revertant count brought about by utilizing an optimal amount of S9.

EXAMPLES 2–15

Thirteen petroleum hydrocarbon oil samples and a corn oil, all of which had been characterized for carcinogenic activity were assayed for specific mutagenic activity by the method of this invention described above under "preferred embodiments". The samples are described in Table I.

Figure 2:
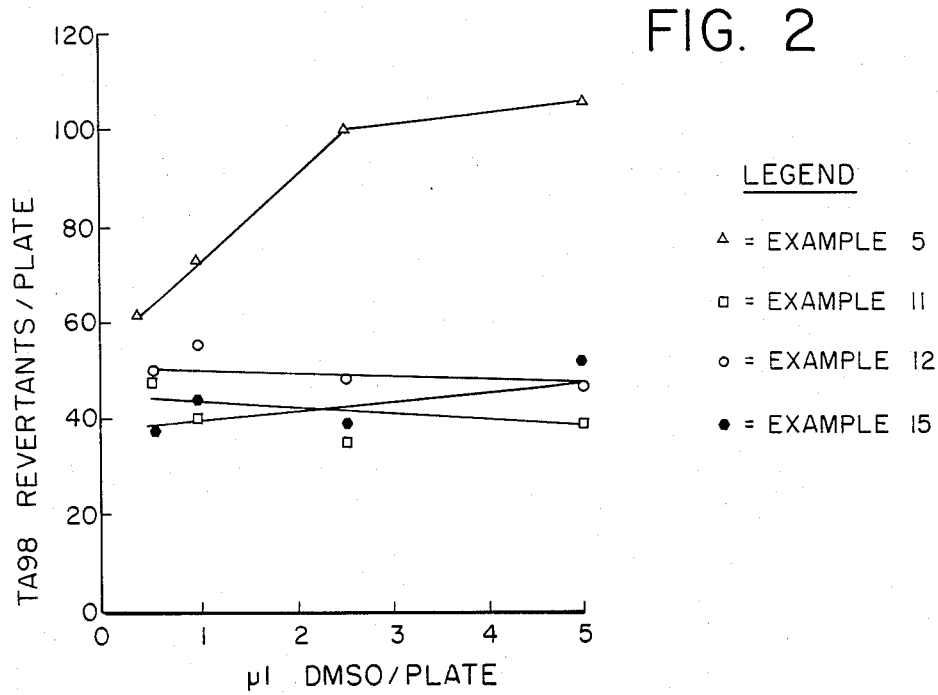
FIG. 2. Dose-response curves.

FIG. 2 of the drawing, which is illustrative, shows the resulting revertant-dosage curves from which specific mutagenic activity was evaluated for Examples 5, 11, 14 and corn oil. Table II shows values for the carcinogenic activity index and the specific mutagenic activity of all samples. FIG. 3 of the drawing shows graphically the correlation between mutagenic activity and carcinogenic activity. Correlation between mutagenic and carcinogenic potencies is very high [0.98 by the least squares method; 0.98 by the Spearman rankorder method, Amer. J. Psychol., 15, 72, (1904)]. In addition, mutagenic activity was detected for all samples which produced detectible carcinogenic activity and no mutagenic activity was detected for the noncarcinogens.

TABLE I

Hydrocarbon Mixtures

| Example | Sample Tested | Chemical Abstract No. |
|---|---|---|
| 2 | Mix of Heavy Catalytic Cracked Distillate & Catalytic Cracked Clarified Oil | 64741-61-3 64741-62-4 |
| 3 | Intermediate Catalytic Cracked Distillate | 64741-60-2 |
| 4 | Light Paraffinic Distillate | 64741-50-0 |
| 5 | Hydrotreated Heavy Naphthenic Distillate | 64742-52-5 |
| 6 | Chemically Neutralized/ Hydrotreated (100″) Heavy Naphthenic Distillate | 64742-34-3/64742-52-5 |
| 7 | Hydrotreated Heavy Naphthenic Distillate | 64742-52-5 |
| 8 | Solvent Refined/Hydrotreated Heavy Naphthenic Distillate | 64741-96-4/64742-52-5 |
| 9 | Solvent Refined/Dewaxed Residual Oil | 64742-01-4/64742-62-7 |
| 10 | Solvent Refined/Hydrotreated (430″) Heavy Paraffinic Distillate | |
| 11 | Solvent Refined/Hydrotreated (400″) Heavy Paraffinic Distillate | 64741-88-4/64742-54-7 |
| 12 | Solvent Refined/Hydrotreated (300″) Heavy Paraffinic Distillate | |
| 13 | Solvent Refined/Hydrotreated Residual Oil | 64742-01-4/64742-57-0 |
| 14 | Solvent Refined/Dewaxed Heavy Paraffinic Distillate | 64741-88-4/64742-65-0 |
| 15 | Corn Oil | |

TABLE II

| | Results | |
|---|---|---|
| Example | Carcinogenic Activity Index[1] | Mutagenic Activity Index[2] |
| 2 | 88 | 55.8 |
| 3 | 50 | 25.3 |
| 4 | 43 | 19.5 |
| 5 | 20 | 20.0 |
| 6 | 19 | 9.0 |
| 7 | 17 | 6.5 |
| 8 | 0 | 0 |
| 9 | 0 | 0 |
| 10 | 0 | 1.4 |
| 11 | 0 | 0 |
| 12 | 0 | 0 |
| 13 | 0 | 1.0 |
| 14 | 0 | 0 |
| 15 | 0 | 0 |

[1]Carcinogenic Activity Index = Total number of tumors ÷ Σ cumulative doses required to produce each observed tumor × $10^5$.
[2]Specific Mutagenic Activity = Slopes of linear portions of dose response curves in FIG. 2, reported as revertants/μl.

EXAMPLE 16

This example illustrates the use of induced hamster liver S9 is the method of this invention. A hydrocarbon mixture known to be weakly carcinogenic (Sample No. 6, Tables I and II) was evaluated by the method of this invention using the same dosage of S9 as was used for rat liver S9. As shown in Table III, there is a significant increase in the sensitivity of the test even though an independent evaluation of the optimal level of hamster S9 was not made.

TABLE III

| | | TA98 Revertants/Plate | | |
|---|---|---|---|---|
| Hydrocarbon Mixture | Dose per Plate | 400 ul Rat S9 | 400 ul Hamster S9 | 400 ul Hamster S9 +2xNADP* |
| Sample #6 | 10 ul oil eqivalent | 99 | 134 | 157 |
| DMSO | 50 ul | 23 | 30 | 25 |
| 2-aminoanthracene | 2 ug | 313 | 639 | 977 |
| Benzo[a]pyrene | 5 ug | 402 | 327 | 478 |

*Nicotinamide adenine dinucleotide phosphate = 8 mM.

What is claimed is:

1. A method for evaluating the potenial carcinogenic activity of a hydrocarbon mixture, which method comprises:
   extracting the hydrocarbon mixture with a solvent effective for removing mutagenic compounds from said mixture;
   subjecting an inoculum of a histidine deficient mutant strain of *Salmonella typhimurium* to incubation in the presence of a sample of said extract and, as metabolic activator, an optimal amount of induced liver homogenate; and
   determining the revertant colonies so produced.

2. The method described in claim 1 wherein said solvent is DMSO, said mutant strain is *Salmonella typhimurium* TA98, and said liver homogenate is Aroclor 1254-induced rat S9.

3. The method described in claim 2 wherein several different size samples of said extract are incubated and said evaluation is made form the linear portion of the dose-response curve.

4. The method described in claim 1 wherein said solvent is DMSO, said mutant strain is *Salmonella typhimurium* TA98, and said liver homogenate is Aroclor 1254-induced hamster S9.

5. The method described in claim 4 wherein several different size of said extract are incubated and said evaluation is made from the linear portion of the dose-response curve.

6. The method described in claim 1 wherein said hydrocarbon mixture is of petroleum origin.

7. The method described in claim 2 wherein said hydrocarbon mixture is of petroleum origin.

8. The method described in claim 3 wherein said hydrocarbon mixture is of petroleum origin.

9. The method described in claim 4 wherein said hydrocarbon mixture is of petroleum origin.

10. The method described in claim 5 wherein said hydrocarbon mixture is of petroleum origin.

11. The method described in claim 1 wherein said solvent is selected from the group consisting of DMSO, 1-methyl-2-pyrollidinone and N,N-dimethylformamide, said mutant strain is selected from the group consisting of *Salmonella typhimurium* TA98 and TA100, and said induced liver homogenate is selected from the group consisting of rat liver S9 and hamster liver S9 induced by Aroclor 1254.

* * * * *

UNITED STATES PATENT AND TRADEMARK OFFICE
CERTIFICATE OF CORRECTION

PATENT NO. : 4,499,187

DATED : February 12, 1985

INVENTOR(S) : Gary R. Blackburn, Carl R. Mackerer and Ceinwen A. Schreiner

It is certified that error appears in the above-identified patent and that said Letters Patent is hereby corrected as shown below:

Col. 1, line 20, "exposure of produce" should be --exposure to produce--.

Col. 3, line 24, "increase on revertant" should be --increase in revertant--.

Signed and Sealed this

Twenty-third Day of July 1985

[SEAL]

Attest:

DONALD J. QUIGG

Attesting Officer     Acting Commissioner of Patents and Trademarks

Disclaimer and Dedication 4,499,187.—*Gary R. Blackburn*, Washington's Crossing, Pa., *Carl R. Mackerer*, Pennington, N.J., and *Ceinwen A. Schreiner*, Newtown, Pa. METHOD FOR EVALUATING MUTAGENICITY. Patent dated Feb. 12, 1985. Disclaimer and Dedication filed Oct. 1, 1985, by the assignee, *Mobil Oil Corp.*

Hereby disclaims and dedicates to the Public the entire remaining term of said patent.

[*Official Gazette December 10, 1985.*]